(12) United States Patent
Lee

(10) Patent No.: US 12,098,069 B2
(45) Date of Patent: Sep. 24, 2024

(54) METHOD FOR MANUFACTURING IMPLANTABLE ELECTRODES AND ELECTRODES MADE BY SUCH METHODS

(71) Applicant: Sangwoo Lee, Ann Arbor, MI (US)

(72) Inventor: Sangwoo Lee, Ann Arbor, MI (US)

(73) Assignee: Minyoung Koo, Ann Arbor, MI (US)

( * ) Notice: Subject to any disclaimer, the term of this patent is extended or adjusted under 35 U.S.C. 154(b) by 340 days.

(21) Appl. No.: 17/540,750

(22) Filed: Dec. 2, 2021

(65) Prior Publication Data

US 2023/0174372 A1 Jun. 8, 2023

(51) Int. Cl.
*B81C 1/00* (2006.01)
*A61B 5/293* (2021.01)
*B81B 1/00* (2006.01)
*A61N 1/05* (2006.01)

(52) U.S. Cl.
CPC .......... *B81C 1/00111* (2013.01); *A61B 5/293* (2021.01); *B81B 1/008* (2013.01); *A61B 2562/125* (2013.01); *A61N 1/0529* (2013.01); *B81B 2201/055* (2013.01); *B81B 2203/0361* (2013.01); *B81B 2203/04* (2013.01); *B81C 2201/0133* (2013.01)

(58) Field of Classification Search
CPC .. A61B 5/293; A61B 5/24; A61B 5/25; A61B 2562/125; A61B 2562/12; A61B 2562/0209; A61B 2562/187; A61N 1/0529; A61N 1/05; A61N 1/0526; A61N 1/0565; B81B 1/008; B81B 1/00; B81B 1/006; B81B 2201/055; B81B 2203/0361; B81B 2203/04; B81C 1/00111; B81C 1/00; B81C 1/00166; B81C 2201/0133; B81C 2201/013; H01L 21/308; H01L 21/02527; H01L 21/02274; H01L 21/0212; H01L 21/3127
See application file for complete search history.

(56) References Cited

U.S. PATENT DOCUMENTS

| | | | | |
|---|---|---|---|---|
| 7,790,493 | B2 * | 9/2010 | Wise | H01L 21/4846 438/83 |
| 8,195,267 | B2 * | 6/2012 | Seymour | A61B 5/24 607/116 |
| 8,350,578 | B2 * | 1/2013 | Sadek | A61B 5/24 324/633 |
| 8,355,768 | B2 * | 1/2013 | Masmanidis | A61B 5/291 607/116 |
| 8,821,560 | B2 * | 9/2014 | Yoon | A61N 5/0622 607/92 |
| 9,247,889 | B2 | 2/2016 | Yoon et al. | |
| 9,801,559 | B2 * | 10/2017 | Jamieson | A61B 5/0084 |
| 10,285,605 | B2 | 5/2019 | Jamieson et al. | |
| 10,856,764 | B2 * | 12/2020 | Dayeh | B81B 1/00 |

(Continued)

OTHER PUBLICATIONS

A microfabricated 3D-sharpened silicon shuttle for insertion J Neural Eng. 16 066021 (Year: 2019).*

(Continued)

*Primary Examiner* — Nikolay K Yushin

(57) ABSTRACT

A method of manufacturing a plurality of neural probes from a silicon wafer in which after neural probes are formed on one side of a silicon wafer, the other side of the silicon wafter is subject to a dicing process that separates and adjusts the thickness of the neural probes.

20 Claims, 6 Drawing Sheets

(56) References Cited

U.S. PATENT DOCUMENTS

| | | | | |
|---|---|---|---|---|
| 2007/0007240 A1* | 1/2007 | Wise | ............... | H01L 24/24 |
| | | | | 156/247 |
| 2009/0177144 A1* | 7/2009 | Masmanidis | ......... | A61B 5/291 |
| | | | | 600/378 |
| 2009/0301994 A1* | 12/2009 | Bhandari | ............... | A61B 5/685 |
| | | | | 216/11 |
| 2010/0145422 A1* | 6/2010 | Seymour | ................. | A61N 1/05 |
| | | | | 600/377 |
| 2010/0219914 A1* | 9/2010 | Sadek | ................. | A61B 5/24 |
| | | | | 333/197 |
| 2012/0172952 A1* | 7/2012 | Yoon | .................. | A61N 5/0622 |
| | | | | 216/11 |
| 2013/0030274 A1* | 1/2013 | Jamieson | ............. | A61B 5/0084 |
| | | | | 600/377 |
| 2013/0072808 A1* | 3/2013 | Neves | .................. | A61B 5/293 |
| | | | | 29/874 |
| 2014/0057411 A1* | 2/2014 | Hoang | ................ | H01L 21/563 |
| | | | | 438/460 |
| 2017/0231518 A1* | 8/2017 | Dayeh | ................ | B81C 1/00111 |
| | | | | 600/544 |
| 2021/0240076 A1* | 8/2021 | Im | ....................... | A61N 1/0531 |
| 2022/0157704 A1* | 5/2022 | Hiblot | .................. | A61B 5/263 |
| 2023/0025444 A1* | 1/2023 | Gleick | ................ | H01L 21/308 |

OTHER PUBLICATIONS

Joo et al. "A microfabricated, 3D-sharpened silicon shuttle for insertion of flexible electrode array through dura mater into brain", 2019, J. Neural. Eng., vol. 16, 066021, pp. 1-14, published Oct. 29, 2019 (Year: 2019).*

* cited by examiner

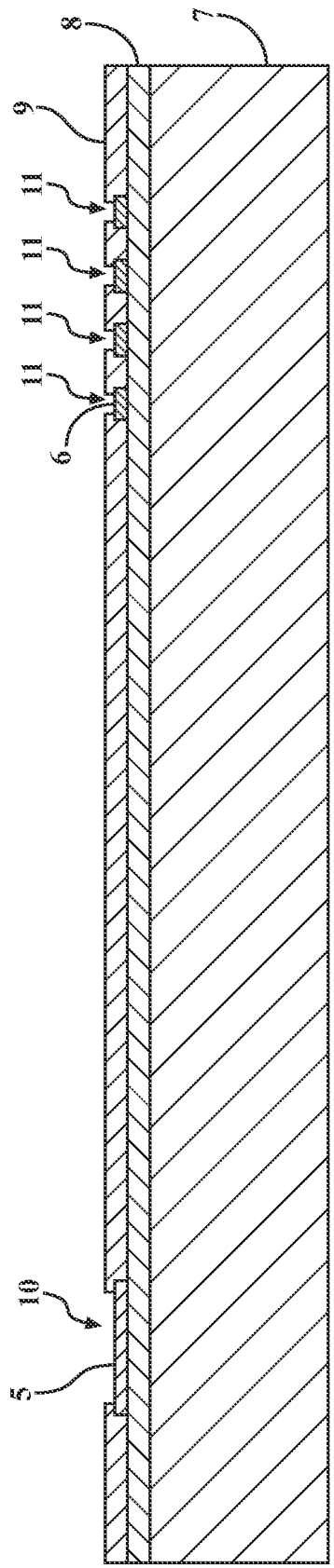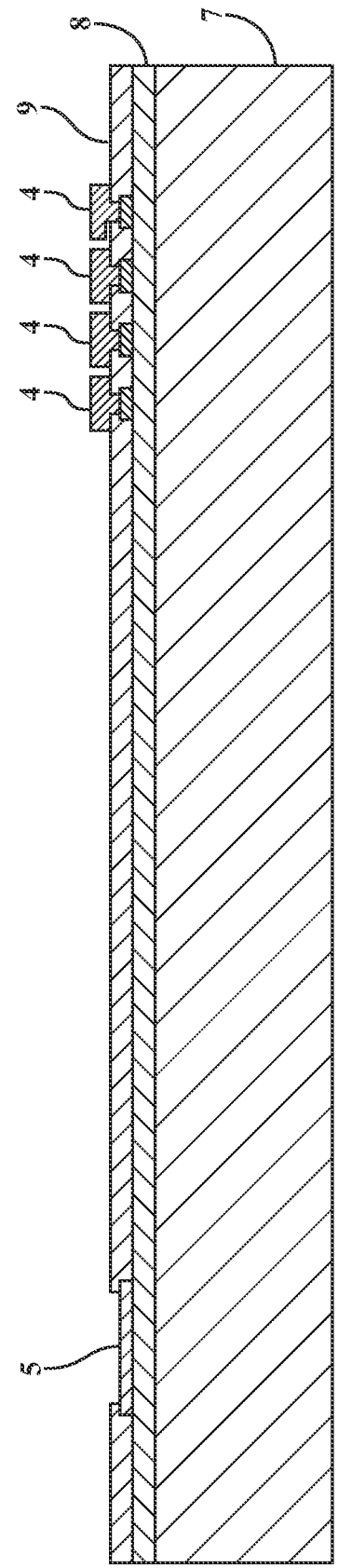

METHOD FOR MANUFACTURING IMPLANTABLE ELECTRODES AND ELECTRODES MADE BY SUCH METHODS

BACKGROUND

The present invention relates generally to neural probes and methods for manufacturing neural probes from silicon wafer.

Neural probes are used to study and understand the functioning of networks of biological neurons of different subjects' brains. In use, neural probes are implanted in different areas of the brain and used to record and/or stimulate specific sites in the brain. Neural probes are currently used in many clinical settings for diagnosis of brain diseases such as seizers, epilepsy, migraines, Alzheimer's, and dementia. For example, in the case of seizers neural probes can be used to locate the area of a subject's brain which triggers seizers by detecting tiny voltage changes as neurons fire nearby. Treatment can then involve monitoring medication results or removal of effected areas. Other research involves using neural probes to assist paralyzed patients by allowing them to operate computers or robots using their neural activity.

Silicon probes made with Micro-Electromechanical Systems (MEMS) fabrication were first introduced by Ken Wise and Jim Angell at Stanford in 1969. Ken Wise's group at the University of Michigan subsequently developed a series of silicon probes and probe arrays with multi-site electrodes. The Michigan probes are made through a wet etch step that stops on boron-doped Si and necks the shank thickness down to around 15 µm. In more recent work, Si Deep reactive-ion etching (DRIE) has been used to make Si probes without the boron etch stop.

A 2D probe array was developed at the University of Utah in 1991, known as the Utah Electrode Array (UEA). The shanks in the UEA are made by sawing grooves into the substrate to form needles followed by a silicon wet etch to smooth the sidewalls and sharpen the needles.

U.S. Pat. No. 10,285,605 to Jamieson et al. and U.S. Pat. No. 9,247,889 to Yoon et al. disclose neural probes with integrated optical stimulation capabilities The present invention provides neural probes and methods for manufacturing neural probes from silicon wafers.

BRIEF SUMMARY

According to various features, characteristics and embodiments of the present invention which will become apparent as the description thereof proceeds, the present invention provides a method for manufacturing neural probes from a silicon wafer which comprises:

providing a silicon wafer having a top side and a back side;

determining a desired shape of neural probes to be made from the silicon wafer, said desired shape including a backend and at least one shank extending outward from the backend;

providing at least one microelectrode on the shank and an equal amount of bonding pads on the backend and interconnects between pairs of the at least one microelectrode and bonding pads, the bonding pads and interconnects being provided on a first electrical insulating layer provided on the top side of the silicon wafer and the microelectrodes being provided on a second electrical insulating layer provided on the first electrical insulating layer;

etching through said first and second insulating layers and a top portion of the top side of the silicon wafer in a pattern that corresponds to the desired shape of the neural probe; and dicing the back side of the silicon wafer to form a neural probe having the desired shape with the shank having a predetermined thickness.

The present invention further provides an improvement in a method of manufacturing neural probes from a silicon wafer in which a plurality of neural probes having backends and shanks are pattered on one side of a silicon wafer, wherein the individual patterned neural probes are separated by a dicing the opposite side of the silicon wafer.

The neural probes can have a single or multiple shanks that can extend outward from the lower edges of the backends at any desired locations.

The shanks can have a thickness of from about 10 µm to about 100 µm and lengths of from about 1 mm to about 20 mm.

The backends can have uniform or non-uniform thicknesses based on the alignment and number of dicing lanes used during the dicing of the back side of the silicon wafer.

BRIEF DESCRIPTION OF THE DRAWINGS

The present invention will be described with reference to the attached drawings which are given as non-limiting examples only, in which:

FIG. 4 is a cross-sectional view taken along section line A-A in FIG. 1 that illustrates the third step in a neural probe manufacturing process according to the present invention.

FIG. 5 is a cross-sectional view taken along section line A-A in FIG. 1 that illustrates the fourth step in a neural probe manufacturing process according to the present invention.

DETAILED DESCRIPTION OF THE DRAWINGS AND THE PRESENTLY PREFERRED EMBODIMENTS

The neural probes of the present invention are manufactured from silicon wafers and include backends and one of more shanks that extend from a lower side edge of the backends. The shank(s) can extend outward from the lower edge of the backends near the sides of the backends or from any position between the sides of the backends.

The shanks are provided with one or more spaced apart microelectrodes and the backends are provided with a similar number of bonding pads. Electrically conductive interconnects connect between the microelectrodes and the bonding pads. The interconnects and bonding pads are made from a conductive material, which may include one or more metals including but not limited to gold, iridium, or platinum. During use output leads and be connected to the bonding pads for processing signals detected by the microelectrodes and/or sending stimulating current to the microelectrodes.

The lengths of the shanks can from about 5 mm to about 10 mm or longer. The widths of the shanks can be from about 30 µm to about 300 µm. The thickness of the shanks can be from about 30 µm to about 50 µm. The number of microelectrodes can range from up to 512 or more. The backends can have a generally rectangular shape or any desired shape and can have uniform or nonuniform thickness with a minimum thickness being the same as the thinnest shank which extends outward therefrom.

Figure 1:
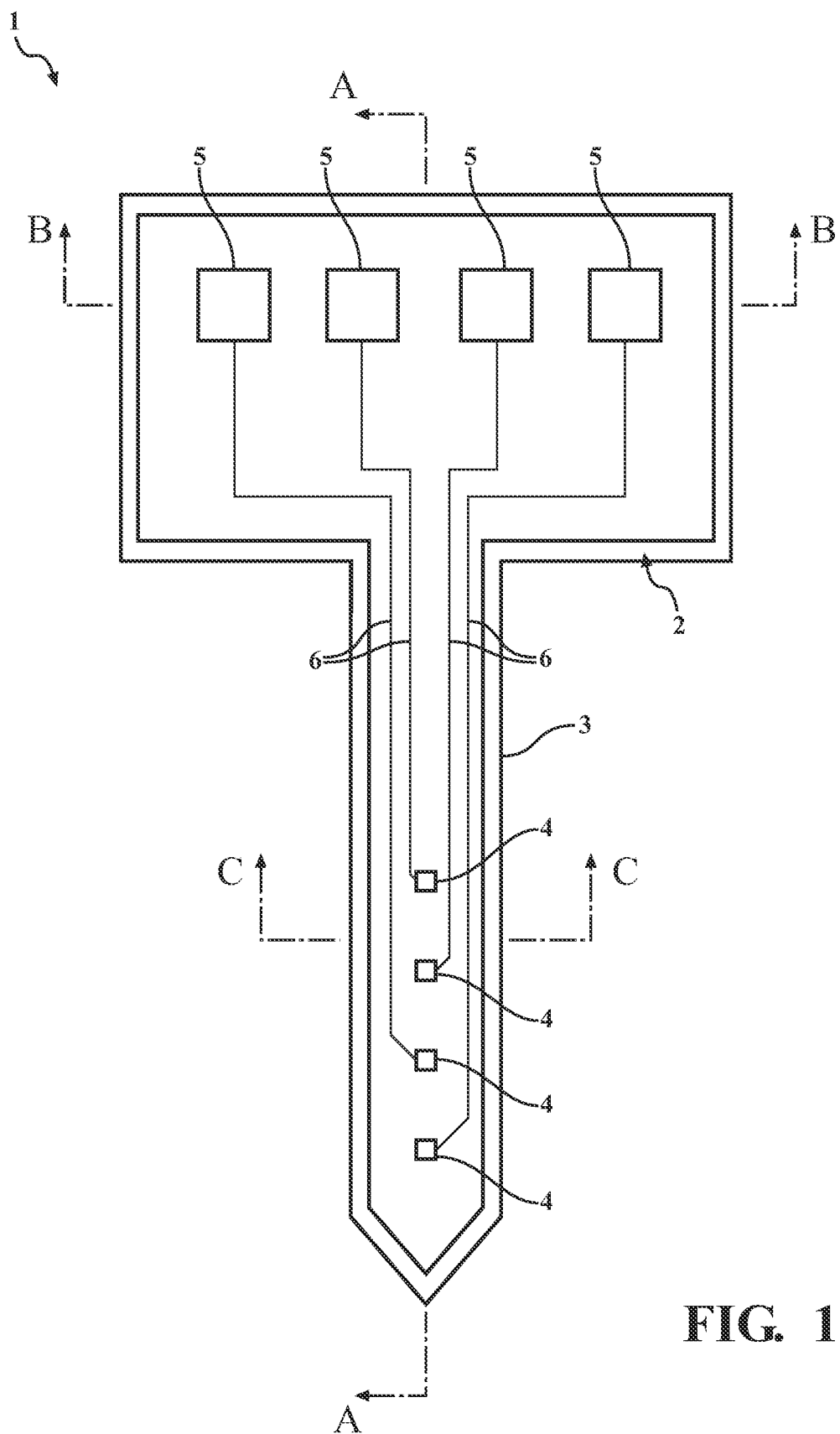
FIG. 1 is a top view of a neural probe according to one embodiment of the present invention.

FIG. 1 is a top view of a neural probe according to one embodiment of the present invention.

The neural probe 1 shown in FIG. 1 includes a backend 2 with a shank 3 extending outward from the middle of the backend 2. A plurality of spaced apart microelectrodes 4 are provided on the shank 3. The backend 2 includes plurality of bonding pads 5 to which output leads can be connected for processing signals detected by the microelectrodes and/or sending stimulation current to the microelectrodes. Electrically conductive interconnects 6 connect between the microelectrodes 4 and the bonding pads 5.

The backend 2 in FIG. 1 has a generally rectangular shape with the shank 3 extending outward form the middle. In other embodiments of the neural probes, one or more shanks can be provided which extend outward from any from any location from the lower portion of the backend 2. In addition, the backend 2 can have any desired shape other that the rectangular shape shown.

The distal end of the shank 3 in FIG. 1 has a pointed shape. In other embodiments the distal end of the shank 3 can be flat or have an angular shape.

While the neural probe 1 in FIG. 1 has four microelectrodes 4 and four bonding pads 5, the number of microelectrodes 4 and bonding pads 5 that can be used is only limited to how small the microelectrodes 4 and bonding pads 5 can be made and the surface area of the shank 3. The number of microelectrodes 4 and bonding pads 5 can range up to about 512 or more.

Figure 2:
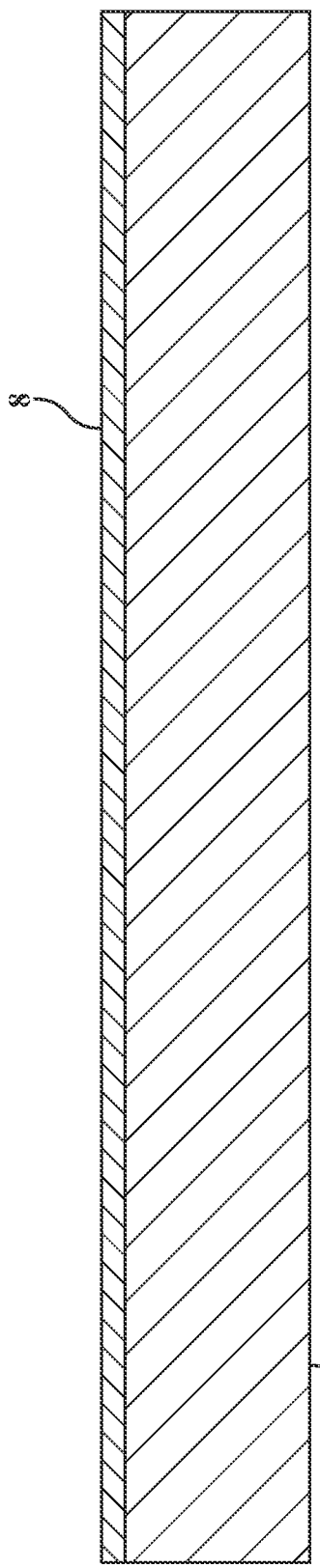
FIG. 2 is a cross-sectional view taken along section line A-A in FIG. 1 that illustrates an initial step in a neural probe manufacturing process according to the present invention.

FIG. 2 is a cross-sectional view taken along section line A-A in FIG. 1 that illustrates an initial step in a neural probe manufacturing process according to the present invention.

The neural probes of the present invention are manufactured from a silicon wafer in a manner that manufactures many neural probes at a time-up to as many that can be made from a standard silicon wafer that can have a diameter of 450 mm or 300 mm or less and have a thickness of from about 775 µm to about 925 µm. Accordingly, in FIG. 2 the silicon base layer 7 is small portion of a silicon wafer.

In the initial manufacturing step, an electrical insulating layer 8 is formed on the top surface of the silicon base layer 7. The insulating layer 8 can be made from silicon dioxide ($SiO_2$) that can be formed by thermal oxidation or by chemical vapor deposition (CVD). The insulating layer 8 generally has a thickness of from about 0.1 µm to about 2 µm or more.

Figure 3:
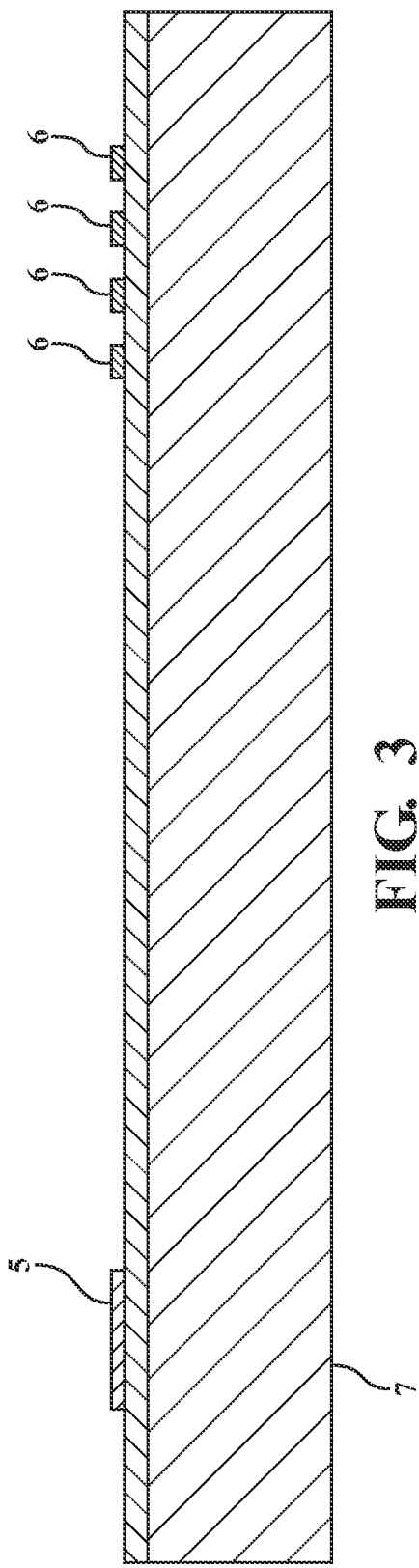
FIG. 3 is a cross-sectional view taken along section line A-A in FIG. 1 that illustrates the second step in a neural probe manufacturing process according to the present invention.

FIG. 3 is a cross-sectional view taken along section line A-A in FIG. 1 that illustrates the second step in a neural probe manufacturing process according to the present invention.

In FIG. 3 the bonding pads 5 and portions of the interconnects 6 that will connect and/or underlie the microelectrodes 4 are formed on the insolating layer 8 by a metal sputtering process using a mask. As noted above, the bonding pads 5 and interconnects 6 can be made from a conductive material, which may include one or more metals including but not limited to gold, iridium, or platinum.

FIG. 4 is a cross-sectional view taken along section line A-A in FIG. 1 that illustrates the third step in a neural probe manufacturing process according to the present invention.

In FIG. 4 a second patterned electrical insulating layer 9 is formed over the interconnects 6 which is formed with openings 10 above the bonding pads 5 and openings 11 above the ends of the portions of the interconnects 6 that will connect and/or underlie the microelectrodes 4. This second insulating layer 9 can be formed by from silicon dioxide ($SiO_2$) and applied by a chemical vapor deposition (CVD) process using a mask.

FIG. 5 is a cross-sectional view taken along section line A-A in FIG. 1 that illustrates the fourth step in a neural probe manufacturing process according to the present invention.

In FIG. 5 microelectrodes 4 are formed which extend through the openings 11 to the ends of the interconnects 6. As shown, the microelectrodes 4 can also extend over the surface of the second insulating layer 9 at the periphery of the openings 11 if desired. The microelectrodes 4 can be formed using a chemical vapor deposition (CVD) process and can be formed from one or more metals including but not limited to gold, iridium, or platinum. In an alternative embodiments, the microelectrodes 4 could be formed on the first insulating layer 8, in electrical contact with the interconnects 6 and provided at the bottoms of openings 11, or in openings 11 with or without extending above the top surface of the second insulating layer.

Figure 6A:
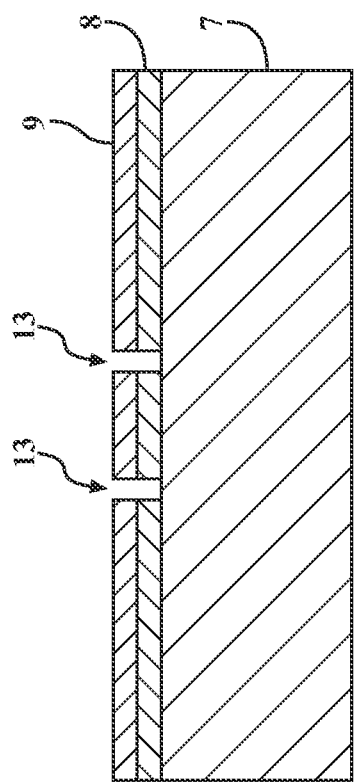
FIGS. 6a and 6b are a cross-sectional view of the neural probe taken along section lines B-B and C-C in FIG. 1 respectively that show how the insulating layers shown in FIG. 5 are etched to define the shape of the final neural probe.
Figure 6B:
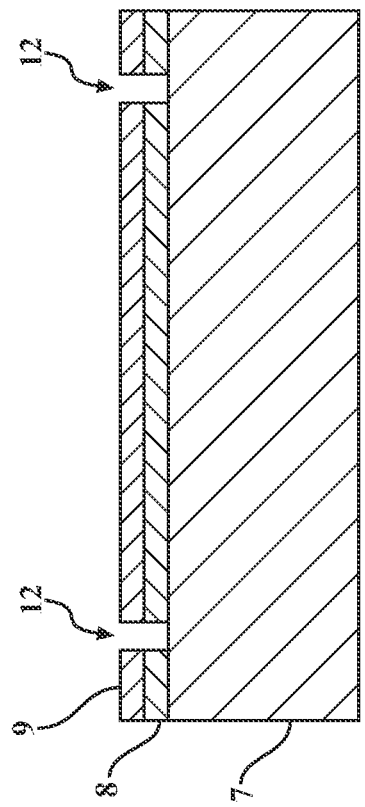

FIGS. 6a and 6b are a cross-sectional view of the neural probe taken along section lines B-B and C-C in FIG. 1 respectively that show how the insulating layers 8 and 9 shown in FIG. 5 are etched to define the shape of the final neural probe 1. In FIGS. 6a, 6b, 7a and 7b the microelectrodes 4, bonding pads 5 and interconnects 6 omitted so as to simplify the description of the process steps.

As shown in FIGS. 6a and 6b, insulating layers 8 and 9 are etched down to the silicon base layer 7. The etching of insulating layers 8 and 9 can be performed using a mask and a buffered Oxide Etch (BOE) etch solution or just hydrofluoric acid. The etched areas 12 shown in FIG. 6a will define the peripheral side edges of the backend 2 of the final neural probe 1 as will be understood as the description of the present invention proceeds. The etched areas 13 shown in FIG. 6b will define the peripheral side edges of the shank 3 of the final neural probe 1 as will be understood as the description of the present invention proceeds.

While not shown, it is understood that the upper and lower peripheral edges of the backend of the final neural probe will be formed by etching the insulating layers 8 and 9 in a similar manner.

Figure 7A:
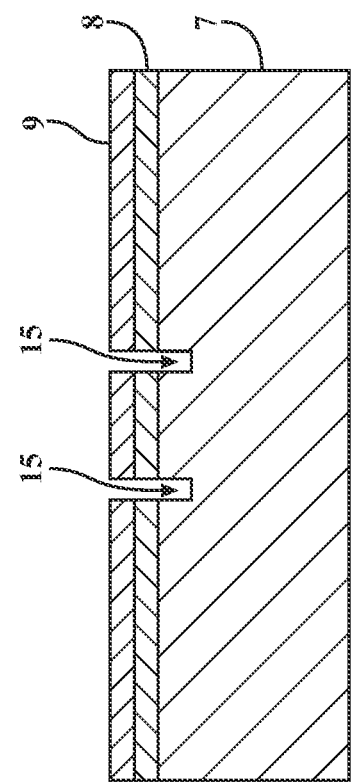
FIGS. 7a and 7b are a cross-sectional view of the neural probe taken along section lines B-B and C-C in FIG. 1 respectively that show how the etched out portion of the insulating layers is extended into the upper portion of the silicon base layer.
Figure 7B:
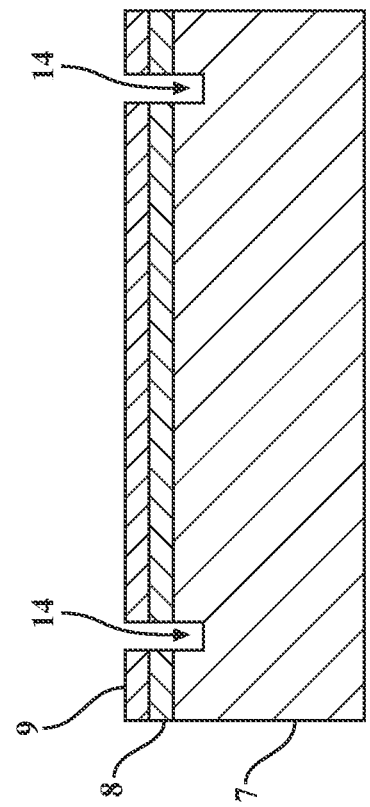

FIGS. 7a and 7b are a cross-sectional view of the neural probe taken along section lines B-B and C-C in FIG. 1 respectively that show how the etched out portion of the insulating layers 8 and 9 is extended into the upper portion of the silicon base layer 7 by an etching process using potassium hydroxide and a mask. The upper portion of the silicon base layer 7 can be etched to a depth of about 80 μm or greater. The etched areas 14 shown in FIG. 7a will define the peripheral side edges of the backend 2 of the final neural probe 1 as will be understood as the description of the present invention proceeds. The etched areas 15 shown in FIG. 7b will define the peripheral side edges of the shank 3 of the final neural probe 1 as will be understood as the description of the present invention proceeds.

While not shown, it is understood that the upper and lower peripheral edges of the backend of the final neural probe will be formed by etching the top portion of the silicon wafer 7 in a similar manner.

Figure 8:
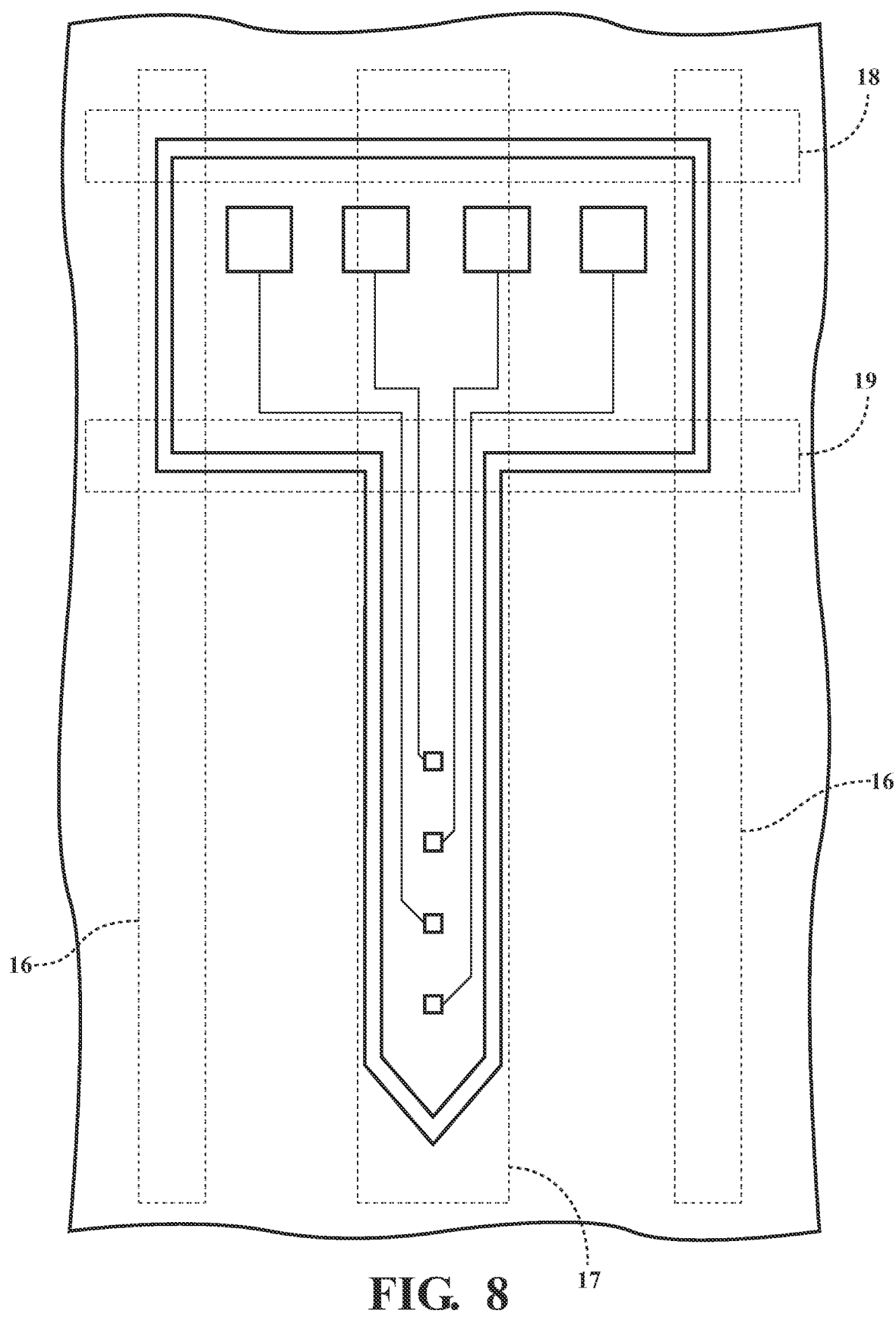
FIG. 8 is a top view that shows diced areas or dicing lanes that are used to form the final neural probes.

FIG. 8 is a top view that shows diced areas or dicing lanes that are used to form the final neural probes.

Figure 9A:
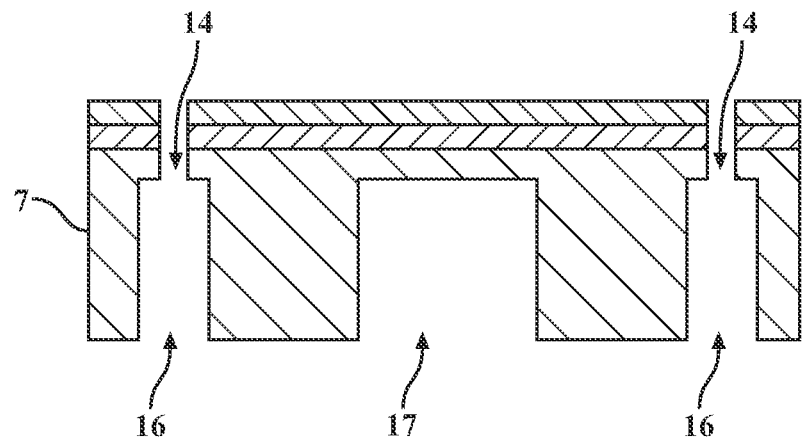
FIGS. 9a and 9b are a cross-sectional views of the neural probe taken along section lines B-B and C-C in FIG. 8 respectively that show how dicing areas or dicing lanes are aligned to form the final neural probes.
Figure 9B:
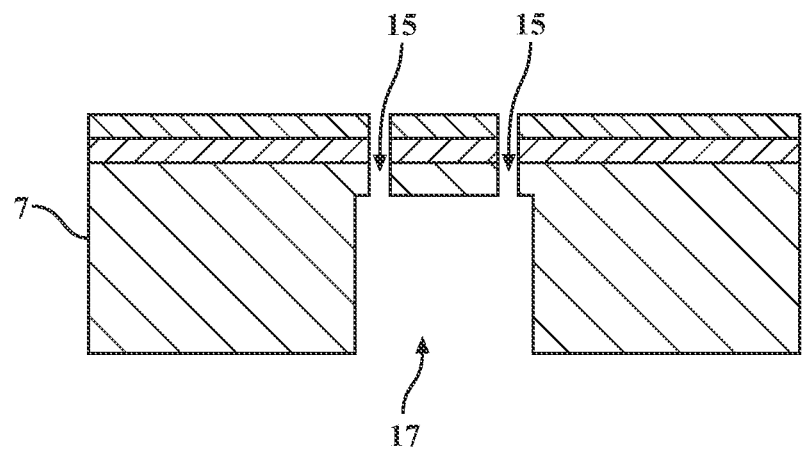

FIGS. 9a and 9b are a cross-sectional views of the neural probe taken along section lines B-B and C-C in FIG. 8 respectively that show how dicing areas or dicing lanes are aligned to form the final neural probes.

After the etching processes discussed above in reference to FIGS. 6a, 6b, 7a and 7a are finished, dicing tape is applied to the top surface of the silicon wafer from which a plurality of the neural probes are manufactured and used to mount the silicon water to a dicing table so that the silicon base layer 7 is on top.

As show in FIGS. 8 and 9a, the back side of the silicon wafer is diced along peripheral dicing lanes 16 that intersect the etched areas 14 shown in FIG. 7a. Likewise, as shown in FIGS. 8 and 9b, the back side of the silicon wafer is diced along a center dicing lane 17 that intersects the etched areas 15 shown in FIG. 7b.

As also shown in FIG. 8, dicing lanes 18 and 19 are formed along the upper and lower peripheral edges of the backend 2 which intersect similarly located etch areas of the silicon wafer.

The final thickness of the shank 3 of the neural probe 1 is determined by the dicing step when the silicon wafer is diced along dicing lane 17. The kerf of the dicing blade used in the dicing step is selected to correspond to a desired shank width (with etched areas 13 in the insulating layers 8 and 9, and etched areas 15 in the upper portion of the silicon base layer 7 being appropriately spaced apart and aligned). Dicing can be performed with dicing blades having different kerfs After the dicing shown in FIGS. 8, 9a and 9b is complete, dicing tape is applied to the back side of the silicon wafer and the dicing tape is removed from the front side of the silicon wafer so that the individually manufactured neural probes can be picked up for assembly.

As shown in FIGS. 8 and 9a, the thickness of the backend of the final neural probes is not uniform due to the locations of the dicing lanes 16 and 17, and the space between the dicing lanes 16 and 17. If desired, additional dicing lanes could be used to make the thickness of the backend uniform.

The manufacturing steps described herein with reference to FIGS. 2-9b can be varied and adapted to manufacture neural probes that have different shapes that the neural probe shown in FIG. 1.

For embodiments in which the location and the number of shanks is different, the pattern for etching of the insulating layers and dicing of the back of the backside of the silicon wafer can be adjusted to achieve the final shape of the desired neural probes. The same or different shaped neural probes can be patterned and formed from a single silicon wafer, including neural probes having shanks located at different positions from the backsides, different numbers of shanks, shanks having different lengths and/or widths and/or thicknesses and neural probes having different numbers of microelectrodes and bonding pads.

The processes for forming the insulating layers and etching the insulating layers and the top portion of the silicon base layer can include those processes noted above as well as any conventional known processes known and used in the art of semiconductor manufacturing or MEMS.

Although the present invention has been described with reference to particular means, materials and embodiments, from the foregoing description, one skilled in the art can easily ascertain the essential characteristics of the present invention and various changes and modifications can be made to adapt the various uses and characteristics without departing from the spirit and scope of the present invention as described above and set forth in the attached claims.

The invention claimed is:

1. A method of manufacturing neural probes from a silicon wafer which comprises:
    providing a silicon wafer having a top side and a back side;
    designing a probe shape of neural probes to be made from the silicon wafer, said probe shape including a backend and at least one shank extending outward from the backend;
    providing at least one microelectrode on the shank of the probe shape, providing at least one bonding pad on the backend of the probe shape, and providing at least one interconnect, at least one interconnect connecting each microelectrode and each bonding pad, the number of microelectrodes, the number of bonding pads, and the number of interconnects being equal, the at least one bonding pad and the at least one interconnect being provided on a first electrical insulating layer provided on the top side of the silicon wafer and the at least one microelectrode being provided on the first electrical insulating layer or in or on a second electrical insulating layer that is provided on the first electrical insulating layer;
    etching through said first and second insulating layers and a top portion of the top side of the silicon wafer in a pattern that corresponds to the probe shape of the neural probe; and
    dicing the back side of the silicon wafer to form a neural probe having the probe shape with the shank having a thickness.

2. A method for manufacturing neural probes from a silicon wafer according to claim 1, wherein the backend has a uniform thickness.

3. A method for manufacturing neural probes from a silicon wafer according to claim 1, wherein the backend has a non-uniform thickness.

4. A method for manufacturing neural probes from a silicon wafer according to claim 1, wherein the dicing of the back side of the silicon wafer comprises using multiple dicing lanes.

5. A method for manufacturing neural probes from a silicon wafer according to claim 1, wherein the at least one shank has a thickness of from about 10 μm to about 100 μm.

6. A method for manufacturing neural probes from a silicon wafer according to claim 1, wherein the neural probe comprises one shank.

7. A method for manufacturing neural probes from a silicon wafer according to claim 6, wherein the one shank extends outward from a middle area of the backend.

8. A method for manufacturing neural probes from a silicon wafer according to claim 6, wherein the one shank extends outward in line with a side of the backend.

9. A method for manufacturing neural probes from a silicon wafer according to claim 6, wherein the at least one shank comprises two or more shanks.

10. In a method of manufacturing neural probes from a silicon wafer in which a plurality of neural probes having backends and shanks are pattered on one side of a silicon wafer, wherein the shanks of individual ones of the plurality of neural probes are thinned by dicing the opposite side of the silicon wafer.

11. The method of manufacturing neural probes from a silicon wafer according to claim 10, wherein a final thickness of the shanks is achieved by the dicing of the opposite side of the silicon wafer.

12. The method of manufacturing neural probes from a silicon wafer according to claim 10, wherein the neural probes include two or more shanks.

13. The method of manufacturing neural probes from a silicon wafer according to claim 10, wherein individual ones of the plurality of neural probes are separated by dicing the opposite side of the silicon wafer.

14. The method of manufacturing neural probes from a silicon wafer according to claim 10, wherein the backends have non-uniform thicknesses.

15. The method of manufacturing neural probes from a silicon wafer according to claim 10, wherein the dicing of the back side of the silicon wafer comprises using multiple dicing lanes.

16. The method of manufacturing neural probes from a silicon wafer according to claim 10, wherein the shanks have a thickness of from about 10 μm to about 100 μm.

17. The method of manufacturing neural probes from a silicon wafer according to claim 10, wherein the shanks have a length of from about 1 mm to about 20 mm.

18. The method of manufacturing neural probes from a silicon wafer according to claim 10, wherein the neural probes have one shank.

19. The method of manufacturing neural probes from a silicon wafer according to claim 18, wherein the one shank extends outward from a middle area of each backend.

20. The method of manufacturing neural probes from a silicon wafer according to claim 18, wherein the one shank extends outward in line with a side of each backend.

* * * * *